United States Patent
Rubin

(10) Patent No.: US 11,510,951 B2
(45) Date of Patent: *Nov. 29, 2022

(54) HEMP POMACE CO-FERMENTED WITH MYCELIA TO FORM A DIETARY SUPPLEMENT

(71) Applicant: Fermented farmer, llc

(72) Inventor: Jordan Seth Rubin, College Grove, TN (US)

(73) Assignee: Fermented Farmer, LLC, Summertown, TN (US)

( * ) Notice: Subject to any disclaimer, the term of this patent is extended or adjusted under 35 U.S.C. 154(b) by 257 days.

This patent is subject to a terminal disclaimer.

(21) Appl. No.: 16/805,512

(22) Filed: Feb. 28, 2020

(65) Prior Publication Data

US 2021/0106635 A1 Apr. 15, 2021

Related U.S. Application Data

(60) Provisional application No. 62/912,930, filed on Oct. 9, 2019.

(51) Int. Cl.
*A61K 36/06* (2006.01)
*A61K 31/05* (2006.01)
*A61K 31/352* (2006.01)
*A61K 9/20* (2006.01)
*A61K 9/48* (2006.01)
*A61K 36/185* (2006.01)
*A61K 9/14* (2006.01)

(52) U.S. Cl.
CPC .............. *A61K 36/06* (2013.01); *A61K 9/14* (2013.01); *A61K 9/20* (2013.01); *A61K 9/48* (2013.01); *A61K 31/05* (2013.01); *A61K 31/352* (2013.01); *A61K 36/185* (2013.01); *A61K 2236/17* (2013.01); *A61K 2236/19* (2013.01)

(58) Field of Classification Search
None
See application file for complete search history.

(56) References Cited

U.S. PATENT DOCUMENTS

| | | | |
|---|---|---|---|
| 2015/0305249 A1* | 10/2015 | Miller | A01H 15/00 47/1.1 |
| 2017/0020178 A1* | 1/2017 | Rubin | A61K 36/00 |
| 2017/0296602 A1* | 10/2017 | Rubin | A61K 31/352 |
| 2019/0320596 A1* | 10/2019 | Miller | A01H 15/00 |
| 2020/0367548 A1* | 11/2020 | Rubin | A61K 36/00 |
| 2021/0106532 A1* | 4/2021 | Rubin | A61K 31/352 |
| 2021/0106533 A1* | 4/2021 | Rubin | A61K 9/48 |
| 2021/0106637 A1* | 4/2021 | Rubin | A61K 31/05 |
| 2021/0154252 A1* | 5/2021 | Rubin | A61K 36/06 |

FOREIGN PATENT DOCUMENTS

CN 102599004 * 7/2012

OTHER PUBLICATIONS

Shu, H. et al. Agricultural Waste Water Environment Research 87(10)1256-1284, 2015. (Year: 2015).*

* cited by examiner

*Primary Examiner* — Ralph J Gitomer
(74) *Attorney, Agent, or Firm* — Barbara E. Johnson, Esq.

(57) ABSTRACT

The present invention is a cannabidiol oral dosage form including predominantly or exclusively hemp pomace that has been co-fermented with a complex fungi, compounded as a tablet or formulated within a capsule. The dosage forms contain dietary fiber, important to activity as the desired delivery system, having a ratio of at least one part soluble dietary fiber to 30 parts insoluble dietary fiber, and delivers desirable/non hallucinogenic cannabinoids (CBD, CBG) in a ratio of 60:1 up to 120:1 to hallucinogenic cannabinoids (THC).

5 Claims, No Drawings

HEMP POMACE CO-FERMENTED WITH MYCELIA TO FORM A DIETARY SUPPLEMENT

CROSS-REFERENCE TO RELATED APPLICATIONS

This patent application claims priority to, and incorporates herein by reference, U.S. Provisional Patent Application 62/912,930 filed 9 Oct. 2019.

FIELD OF THE INVENTION

The invention pertains to improved CBD (and related cannabinoid) delivery methods and dosage forms.

BACKGROUND OF THE INVENTION

A recognized leader (if not "Father") of modern *Cannabis* chemistry is Raphael Mechoulam, who spoke in April of 2019 to the ICBC International *Cannabis* Business Conference. In recounting his particular interest and history in studying *Cannabis*, he began his keynote address remembering that "In ancient Syria they used *cannabis* for essentially all the things that people use *Cannabis* for today" and that "*Cannabis* was then used over the next couple of thousand years." With *Cannabis* indica, *Cannabis sativa* and *Cannabis ruderalis* having thus had a longtenure as known active agents, The History Channel recently devoted an entire special issue magazine to the story of *Cannabis* throughout the world, indicating (without limitation) that Queen Victoria's physician probably prescribed versions of *Cannabis* medicaments for pain management, and so forth. Mechoulam corroborated this connection of *Cannabis* to royalty in his keynote, explaining that "Dr Russell Reynolds, who was the physician of Queen Victoria in England, used to import [*Cannabis*] from India (European *cannabis* was not good enough for him) because she suffered from migraines." Whereas there are no specific historic references to administration of *Cannabis* to the Queen at that time, Mechoulam points out that "it was obvious who it was for because she was the only patient that he had." With a fast forward to the 2018 "Farm Bill" (Agricultural Improvements Act of 2018, 115th Congress, 2017-2018) the United States law now acknowledges that industrial hemp, a *Cannabis* plant with less than 0.3% tetra hydrocannabinol (THC) is not "marijuana" for the purpose of the Controlled Substances Act. This means that hemp-derived cannabidiol (CBD) and related cannabinoids such as cannabigerol (CBG) and cannabichromene (CBC) can now ostensibly be produced and sold as a consumable agricultural products in the United States, whereas prior to the 2018 Farm Bill hemp could be grown and used in the U.S. only for research purposes under individual states' pilot programs and in certain categories such as clothing, industrial materials and products made from the plant's stalks or seeds. In other words, 2018 was a watershed year for health care providers, consumer packaged goods companies and the pharmaceutical industry, creating for the first time a legal (or nascently legal) domestic source of cannabinoids (primarily CBD)—from U.S.-grown hemp.

This watershed has led to a predictable avalanche of hemp growing, extraction, formulation and processing in the United States, to produce CBD and a myriad of products containing it. As a result, more-retail-cash-registers-than-not offer various CBD products for sale—sometimes many edible offerings such as individually wrapped chocolates containing CBD along with CBD topicals, oils and capsules—and of course online sales are brisk as well. CBD has long been known for its pain relieving, relaxing, sleep supporting, anxiety reducing benefits, rather than intoxicant properties, and sales of CBD containing products have been understandably swift and growing in the U.S. from 2018 to date.

As with any newly popular ingredient, there are opportunities for high quality products as well as those of lesser value and benefit. There are currently reliable, responsible cannabinoid rich hemp growers, manufacturers and, presumably, also formulators and peddlers reminiscent of the "snake oil salesmen" of the American 1800s. This "snake oil" analogy is apt, because Chinese snake oil was a legitimate anti-inflammatory substance for decades if not centuries, prior to faux iterations that appeared later in the U.S. The original Chinese snake oil was made from the oil of the Chinese water snake, which was rich in the omega-3-fatty acids that are known to reduce inflammation. This "snake oil" in its original form was indeed effective as a topical medicament to treat arthritis and bursitis and, eventually, the story and erstwhile product made its way to the United States—if not the omega-3-rich water snake itself, or its curative extract. The point here is that with CBD, as with anything else, responsible sourcing, processing and quality control in manufacturing are the bedrock of any superior pharmaceutically active agent. The pressures of manufacturing in light of a population clamoring for CBD are particularly intense, in world in which side-effect- or addiction-minimized pain management is still an elusive if (not scandal-laden) goal.

It is interesting that, as a general practice regarding naturally-occurring active agents—and particularly those of herbal sources—there seems to be a knee-jerk compulsion to extract the active agent compound from its botanical herb or spice. This is epitomized by extracting and synthesizing digitalis from foxglove, a natural herb, marketed as a pharmaceutical. In theory there is nothing wrong with extraction processes—although in practice there can indeed be negative implications to extraction, in particular as to the molecule(s) to be extracted. Extraction agents such as petroleum or coal-tar derived solvents can create residues or even alter the chemical composition of the sought-after molecule. Worse, beneficial co-factors present in the natural product in this case an herb can be separated from the active agent so as to lose the synergy of administration of the whole herb with it's known and yet-to-be discovered compounds. Even today, when *Cannabis* indica, *Cannabis sativa* and *Cannabis ruderalis* are on the brink of becoming "health food" [so to speak] instead of "Just Say No!" fodder, the temptation seems to be ubiquitous to extract and isolate key constituents within them, in order to obtain their active agent(s) for further commercialization. The question which the present inventor asked, though, was—whether traditional extraction or isolation is the only processing method that can deliver the true benefits of hemp?

SUMMARY OF THE INVENTION

The present medicament and pharmaceutical, nutraceutical and treatment method and method for delivering an active agent, centers on a powdered form of extracted hemp pomace containing cannabinoids including CBD, dietary fiber of a particular ratio, vitamins, minerals, flavonoids, terpenes, fatty acids and amino acids, which powder is blended with other botanical ingredients or compressed into a tablet form for administration to or consumption by an animal or human in need of a reliably sourced CBD (or other cannabinoid) oral dosage form. In particular, such dosage forms specifically include the fermentation products of complex fungi (nutritional or medicinal mushrooms) grown in association with extracted hemp pomace, as well as fungal components of co-fermentation of hemp pomace with complex fungi, and inevitably a certain degree of moisture (water). While the present extracted hemp pomace co-fermented with complex fungi is well suited to use alone, it may be admixed with other ingredients, whether active agents or excipients, fillers or comestible ingredients comprising dietary supplements or functional food ingredients. "Spent extracted hemp biomass" is a co-product of cannabinoid (CBD, CBG etc) extraction—preferably an organic process without the use of toxic solvents or their derivatives. As with all extraction methods and the limited yields one can expect from an extraction process, in fact there is a sizeable fraction of cannabinoids (CBD) remaining in hemp pomace. Even more importantly, however, the CBD/cannabinoid(s) in the hemp pomace contain naturally occurring co-factors, known and currently unknown, including without limitation other cannabinoids, dietary fiber, fatty acids, amino acids, terpenes (see below) and flavonoids, which enhance any or all of delivery, bioavailability and efficacy of the CBD/cannabinoid(s) in vivo. A key part of the present invention inheres in the ability to use predominantly or completely a fungally fermented extracted hemp pomace constituent as the tablet or capsule (or equivalent) ingredient in a CBD/cannabinoid oral dosage form, typically after having been carefully dried and potentially activated through de-carboxylation of cannabinoids. Another key component to the invention is in the engineering of the delivery system, with a beneficial soluble dietary fiber (SDF)/insoluble dietary fiber (IDF) ratio of at least 1:30 SDF/IDF, allowing for effective formulation and delivery of key constituents. Moreover, the process of creating hemp pomace using natural, non toxic forms of extraction, tends to increase the ratio (increasing the percentage) of non hallucinogenic/addictive cannabinoids such as CBD, CBG, CBC to hallucinogenic/addictive cannabinoids, i.e. THC. For example, many native hemp species have a ratio of CBD:THC of 20:1, whereas the process of producing pomace in accordance with this invention results in a CBD:THC ratio of between 60:1 to as high as 100:1. Moreover, as Raphael Mechoulam pointed out in the above-mentioned keynote, many forms of *Cannabis* heretofore underappreciated—such as cannabidiol acid, cannabidiol acid methyl ester—will predictably become of greater interest in the future, due to their increased pain alleviation effects, reduced hallucinogenic effects and so forth. A benefit of extracted hemp pomace is that it constitutes an indigenous matrix within which the remaining naturally occurring cannabinoids can equilibrate into their most stable chemical and physical forms in vivo, poised for further biochemical conversion and derivation by beneficial mushroom culture. The inventive, hemp pomace co-fermented with complex fungi is uniquely suitable for tabletting without further additional additives, diluents or synthetic excipients—or the fermented hemp pomace may be included in standard "hard shell" capsule, mixable powder or other dosage forms known to those skilled in the art.

DETAILED DESCRIPTION OF THE INVENTION

As with popular or over-the-counter dosage forms, particularly for active agents known to control pain, dosing is tantamount to safe and effective treatment. When it comes to CBD, general dosing guidelines suggest that a good starting dose is somewhere in the range of 1-5 mg once or twice a day, for an averaged sized human patient, with possible ethical dosing of up to 20 mg or more taken as often as three times per day. Veterinary dosing is generally pro rata by body mass/weight. As the CBD industry matures, inevitably further dosing guidelines will become available—but as with all active agents a serious challenge is to prevent inadvertent (or intentional) overdose. One benefit of the present co-fermented formulations inheres in the lower cannabinoid (i.e. CBD) concentration of hemp pomace along with synergistic co-factors which provides a more balanced, "whole food" effect with less chance of deleterious side effects. A simultaneous benefit of the co-fermenting hemp pomace with complex fungi is that, whereas the CBD (or other cannabinoid) content has been reduced compared to the native hemp, the ratio of soluble dietary fiber (IDF) to insoluble dietary fiber remains generally the same as in the native hemp. The starting SDF/IDF ratio in extracted hemp pomace, pre-fermentation, is 1:30, that is, for every 1 part of soluble dietary fiber in the hemp pomace, there is also 30 parts insoluble dietary fiber. After fermentation according to this invention, the some of the IDF is not only reduced but results in the creation of some very interesting, and nutritionally and medicinally beneficial, fermentation products such as chitin and other polysaccharides including alpha and beta glucan(s)—leaving nonetheless an SDF/IDF ratio of at least 1:30.

So as is apparent from the above explanation, even though extracted hemp pomace is the co-product of cannabinoid (CBD) extraction, this does not mean that it does not still contain meaningful amounts of cannabinoids, such as CBD. In the analogous case of wine making, after pressing of the fermented grapes, a large portion of the beneficial, natural compounds—such as resveratrol—remain in the grape pomace as has been detailed in published research and prior art. The importance of this analogy is that even hemp pomace resulting from a natural extraction process can be relatively rich in cannabinoids such as CBD, that is, contains on the order of 10-25% or so of the original CBD content of the pre-extraction "native" hemp biomass. All of this can be simply controlled by process monitoring and testing well known in the art.

The importance of the previous paragraph has to do with unit dosage form preparation of extracted hemp pomace. If hemp has, for example, a starting content of 10% CBD, removal of 75-90% of that amount of CBD will yield (say) a 1-2.5% CBD content in the hemp pomace. This means that for every gram of hemp pomace, the intrinsic remaining CBD in the hemp pomace is on the order of 10-25 mg, which is right in the range of a standard unit dosage form and dosing amount. These levels are theoretical and can be monitored and adjusted in real life manufacturing settings. For illustrative purposes, then, if a gram of hemp pomace contains 15 mg of CBD, it is readily possible to formulate 1 mg, 3 gm, 5 mg, 10 mg and even 20 mg CBD dosage forms by selecting the appropriate fraction of a gram of hemp pomace, or possibly slightly more than one gram, per unit dosage form. Larger serving sizes of tablets or capsules can thus contain up to 20 mg CBD while still having a size that can be consumed without difficulty. The ability of hemp pomace (with or without bacterial or fungal fermentation) to be formulated into oral dosage form capsules—or to be tabletted directly without additives—means that creation of dosing per unit is straightforward and well within the skill of the art. In fact, one of the surprisingly beneficial aspects of the present invention is the ability of hemp pomace to be tabletted or otherwise crafted into unit dosage forms without needing additives, or synthetic excipients, fillers or binders.

When the above described extracted hemp pomace is subjected to cofermentation with complex fungi, additional benefits ensue. The additional presence of fungal components and a myriad of fermentation products with the extracted hemp pomace is the main exception, besides moisture, to the inventive premise that overall the dosage form material (apart from a capsule if necessary) is predominantly or completely extracted hemp pomace. So, with the extracted hemp pomace's being is fermented with complex fungi prior to dosage form creation, inclusion of all the co-fermentation products in the dosage form is within the scope of the invention—and of course additional probiotics may be co-formulated with the fungally fermented hemp pomace without prior or concurrent fermentation also.

It almost goes without saying that organically sourced hemp, extracted without hydrocarbon-based or petroleum or coal tar derived solvents, is the best choice for hemp pomace according to the present invention. By using organic hemp and avoiding noxious extraction solvents, the presence of pesticides or other solvent residues or undesirable adulterants in the hemp pomace is reduced to a beneficial minimum. Not only is the reduction of these extraneous contaminants good in and of itself, but the absence of unwanted residues maximizes the original confluence of the indigenous cannabinoids such as CBD with its synergistic co-factors, known (see list above) or unknown.

In creating co-fermented extracted hemp pomace with complex fungi, the process constraints of mycelium culture must be observed, and this sterilization does have an impact on the hemp pomace constituents. For example, a culture medium for complex fungi (in this case the hemp pomace itself) must be sterilized, prior to inoculation of the mycelium to be grown and co-fermented. This sterilization will denature or otherwise obliterate certain constitutes on the hemp pomace, such as indigenous terpenes. However, the fermentation products generated by the complex fungi more than compensate for such losses, overall, in the final fermentation product. The present invention inheres mainly in the cofermentation of hemp pomace with complex fungi as a never before thought of combination. Mushroom fermentation of extracted hemp pomace does a number of very desirable things to the pomace, including without limitation:

preferentially metabolize with/grow on the non nutritive components of hemp pomace, i.e., insoluble fiber fraction (IDF), and convert them to beneficial/nutritive compounds (so whereas the pomace itself is 35% fiber, the mushroom-cultured hemp pomace will have a lower IDF content AND some very interesting fermentation products of that fiber (chitin and alpha and beta glucan polysaccharides as well as other polysaccharides) resulting from the mushroom growth and metabolism);

mushroom culture will tend to activate or potentiate biologically active compounds present in the substrate AND will also tend to make them more bioavailable, within any number of mechanisms including but not limited to solubilization, digestion, encapsulation, or derivatization;

mushroom culture will undoubtedly give a greater panel of constituent compounds and compositions than the starting hemp pomace contained, due to the complicated transformational fermentation that occurs when mushrooms grow; and just as some bacterial growth can create acids and other byproducts that are antifungal, fungal growth can in many cases be antibacterial or yield antibacterial compounds, giving unique benefits to fungal fermentation products for further use as antibacterials at least some of the time.

Hemp pomace thus fermented according to the present invention, and evincing all the above benefits, is typically dried, tabletted or encapsulated into one or more unit dosage forms. Dehydration to a moisture content of below 15%, preferably below 10% and more preferably to 5-6% is important in the creation of the present oral dosage forms. The co-minution may be but need not be to a (small) particle size generally within the range of powders. Generally speaking, co-fermented hemp pomace particles of at least 100 microns in diameter, up to irregularly shaped particles of up to about 5 mm in their longest dimension, are best for tableting or encapsulating according to the present invention. Surprisingly, hemp pomace particles of this size are beneficially self tabletting without added ingredients and with a minimum of compression energy, that is, not enough pressure to generate significant heat. Avoidance of excessive processing also prevents the generation of unwanted heat that can denature cannabinoids (CBD), terpenes or additional cofactors in the hemp pomace. Having said that, however, the administration of hemp pomace as a powder (that is, in traditional powder particle size distributions smaller than 100 microns) and as predominantly the only oral dosage form constituent as described above—is still within the scope of the present invention.

The primary disclosure of this patent application is directed to dosage forms in which contain extracted hemp pomace co-fermented with complex fungi. Having said that, there is a specialized application for hemp pomace, with or without co-fermentation or added probiotic, as a non-predominant dosage form additive, that is, as an excipient, usually as a hardening agent. The properties of hemp pomace are so advantageous for oral dosage form preparation that, even apart from the main embodiment of the invention in which hemp pomace is administered predominantly by itself, hemp pomace is also uniquely useful as a hardening agent and excipient for other oral dosage forms. The hemp pomace used as a hardening agent or pharmaceutical excipient may be employed with or without fermented, or co-formulated, probiotic, such as bacteria or fungus. By the same token, the emphasis in the present disclosure is on hemp pomace, for all the benefits above described, and yet it is equally possible to ferment, or co-formulate, native hemp (that is, not previously extracted) with bacterial or fungal ingredients to achieve similar formulational benefits. In other words, the present invention also embraces bacterial- or fungal-fermented hemp, as well as hemp pomace. One skilled in the art is well able to adjust the dosing parameters discussed above to accommodate the higher constituent amounts, such as CBD, in the native hemp versus the hemp pomace.

Prior to co-fermentation with complex fungi, hemp pomace contains total dietary fiber (TDF) having a ratio of 1 part SDF to 30 parts IDF. As compared to higher SDF-containing botanicals, such as for example oat bran or bananas, a ratio of 1:30 SDF/IDF is a notably low SDF/IDF ratio and, for the purposes of the present invention, this high inclusion of IDF is extremely beneficial to delivery of CBD and other cannabinoids from an oral dosage form. SDF, upon oral administration, tends to create a sol/gel in the gastrointestinal tract, which in turns tends to retain in solution, i.e. binding or suspension, other molecules in its vicinity such as, in this case, cannabinoids. In other contexts, SDF is a highly desirable nutrient, that can even be partially digested by bacteria in the gut, but in the context of a cannabinoid delivery system SDF actually creates a binding system and subsequent removal from the body for an active agent, rather than a true delivery (release) system into the blood stream. By contrast, the high IDF inclusion assures the desirable release of the active agent promptly if not instantly in the stomach or upper gastrointestinal tract. Given this understanding of how the present oral dosage form works, moreover, it may be seen that the present oral composition, although botanical in initial source, is a highly engineered composition and not merely a product of nature at all. With the present oral dosage forms, the cannabinoid content is reduced (compared to native hemp) and yet the SDF/IDF ratio of 1:30, typical of native hemp, enhances delivery due to its high soluble fiber fraction. In fact, the engineering of the hemp into pomace creates a fascinating paradigm—when one realizes both that extraction is NOT always the desired processing and delivery method for hemp and that native hemp may be too high in THC content to be optimally useful as an oral dosage form, hemp pomace becomes a primary, premium product, and in no way a by-product of something else. (Even more interesting, in a world full of controlled-release and sustained-release pharmaceuticals, is the effective "flip" of the controlled release paradigm in the present invention, in that with the present invention the active agent delivery is designed to be instantaneous or at least prompt (not controlled or sustained), but the dosing per unit is deliberately reduced from its native form, rather than concentrated.) With the above understanding, therefore, the following terms are all synonymous: spent hemp pomace; hemp pomace, extracted pomace; extracted biomass; extracted hemp biomass; extracted hemp marc, extracted marc, native marc and native pomace. Moreover, inasmuch as the pomace is the supportable star of hemp extraction, in contrast to an extract, it is appropriate to call the present pomace "Hemp Extract" or "Whole Food Cannabinoid Extract," in the sense that it is the pomace that has been importantly wrested from the native hemp, not the relatively less useful traditional cannabinoid extraction products. Given all of the above, when extracted hemp pomace is co-fermented with complex fungi, the SDF/IDF ratio is preserved overall as an "at least" ratio of 1:30, in the sense that some fraction of the IDF will be reduced by the beneficial fermentation of the fungi with the hemp pomace to create fiber fermentation products as described above. Even so, the action of the fungal fermentation "does not throw off" the beneficial ratio of SDF/IDF significantly, and the inventor estimates that the fungal depolymerization of IDF is on the order of only about 5%—enough to create the new and beneficial fermentation products of interest, but not enough drastically to change the SDF/IDF paradigm in extracted hemp pomace starting material.

Important cannabinoids in hemp pomace are not limited to cannabidiol (CBD). Known significant cannabinoids other than THC include, without limitation, cannabigerol (CBG), cannabidivarin (CBDV), cannabichromene (CBC), cannabinol (CBN) and combinations thereof. Beyond understanding just the various active agents themselves, also, Raphael Mecholaum is well known for having identified "the entourage effect." When it comes to *Cannabis*, some of the effects of "quite a few cannabinoids" are "potentiated by compounds which by themselves had no activity, yet they potentiate the activity of [for example] THC," he points out. Explaining further, he notes that although the entourage effect "is not observed in . . . all effects of cannabinoids, many of them have this 'entourage effect' and so things become very complicated if somebody wants to [use] THC or CBD as an extract, [because] they also need to know what other compounds are present." The current technology harnesses the entourage effect in a novel way, given that not only are the co-fermented hemp pomace materials themselves not extracts (the starting hemp pomace is what is left from previous extraction) the remaining cannabinoids inhere in an in vivo form which encourages and preserves the entourage effect as it occurs in nature and, it is believed, the fungal co-fermentation increases the entourage effect by increasing the panoply of constituents present in and around the cannabinoids. Also, and as is the case with all *Cannabis* horticulture, various strains of hemp tend to present different ratios of these cannabinoids and, in due course, the desired ratios will also inevitably be genetically engineered if not traditionally cross-bred. The ability of fungally co-fermented hemp pomace to serve as a uniquely effective delivery system for any and all cannabinoids and additional beneficial hemp components, typically in reduced amounts compared to their native hemp percentages, will apply to any hemp strain known or developed in the future.

Example 1

A quantity of native hemp is subjected to a traditional extraction of cannabinoids by moderate crushing and extraction of cannabinoids to create a "hemp pomace" which continued to include cannabinoids therein. The extraction may be by ethanol solvent extraction, carbon dioxide solvent extraction, vapor distillation, or flash pasteurization. At this writing, such extraction techniques for hemp (*Cannabis*) are known by those skilled in the art. The resulting pomace is carefully air dried at temperatures lower than 115 degrees Fahrenheit to prevent denaturing of all compounds and compositions in the pomace. A representative dried pomace prepared according to the above method steps contained 6% moisture and certain exemplary specifications listed in the below table.

TABLE 1

| QD252 - Protein - Combustion | Reference | Accreditation | Analysis Completed |
|---|---|---|---|
| | AOAC 990.03; AOAC 992.15 | A2LA ISO/IEC 17025:2005 | Jan. 15, 2020 |
| Parameter | | Result | |
| Protein | | 26.50% | |
| Nitrogen - Combustion | | 4.24% | |
| Protein Factor | | 6.25 | |

| QD250 - Ash | Reference | Accreditation | Analysis Completed |
|---|---|---|---|
| | AOAC 942.05 | A2LA ISO/IEC 17025:2005 | Jan. 15, 2020 |
| Parameter | | Result | |
| Ash | | 17.74% | |

| QD226 - Calories, Calculated | Reference | Accreditation | Analysis Completed |
|---|---|---|---|
| | CFR - Atwater calculation | A2LA ISO/IEC 17025:2005 | Jan. 17, 2020 |
| Parameter | | Result | |
| Calories Calculated | | 323 kcal/100 g | |

TABLE 1-continued

| QD038 - Carbohydrates, | Reference | Accreditation | Analysis Completed |
|---|---|---|---|
| | CFR 21-calc. | A2LA ISO/IEC 17025:2005 | Jan. 17, 2020 |
| Parameter | | Result | |
| Carbohydrates, Calculated | | 46.25% | |
| QD148 - Moisture by Vacuum | Reference | Accreditation | Analysis Completed |
| | AOAC 925.09 | A2LA ISO/IEC 17025:2005 | Jan. 17, 2020 |
| Parameter | | Result | |
| Moisture and Volatiles - Vacuum Oven | | 6.0% | |
| QD251 - Calcium by ICP | Reference | Accreditation | Analysis Completed |
| | AOAC 984.27 mod, 927.02 mod | A2LA ISO/IEC 17025:2005 | Jan. 15, 2020 |

The materials as described in the above table are then sterilized, using heat and pressure, according to known sterilization techniques for mushroom culture. Inoculation of complex fungi are then accomplished by means known in the art, to co-ferment with the above-described hemp pomace any of *Ganoderma lucidum, Ganoderma japonicum, Ganoderma applanatum, Ganoderma Tsugae, Lentinula edodes, Grifola frondosus, Tremella fuciformia, Tremella mesenterica, Cordyceps sinensis, Cordyceps militaris, Hericium erinaceus, Polyporous umbellatus, Scizophylum commune, Fomes fomentaris, Inonotuus obliquus, Lepiota procera, Auricularia auricula, Tuber melanosporum, Tricholoma matsutake, Hericium coralloides, Trametes versicolor, Phellinus linteus, Poria cocos, Antrodia camphorata, Flammulina velutipes, Pleurotus ostreatus, Pleurotus energyii,* or *Agaricus blazeii*. The resulting co-fermentation products, retained in admixture and further dried, cominuted or powdered and formulated into capsules, tablets or other dosage forms, are the gravamen of this invention. The co-fermented fungi and hemp pomace are believed to retain the SDF/IDF ratio of at least 1:30 and it is believed that the fungal co-fermentation reduction of IDF is on the order of about 5%.

Although the technology has been described with particularity above, with reference to specific materials and methods, the invention is only to be limited as is set forth in the following claims.

I claim:

1. A cannabinoid oral dosage form in unit dosage form, consisting essentially of hemp pomace, said hemp pomace further comprising spent extracted hemp biomass, co-fermented with a fungus selected from the group consisting of *Ganoderma lucidum, Ganoderma japonicum, Ganoderma applanatum, Ganoderma Tsugae, Lentinula edodes, Grifola frondosus, Tremella fuciformia, Tremella mesenterica, Cordyceps sinensis, Cordyceps militaris, Hericium erinaceus, Polyporous umbellatus, Scizophylum commune, Fomes fomentaris, Inonotuus obliquus, Lepiota procera, Auricularia auricula, Tuber melanosporum, Tricholoma matsutake, Hericium coralloides, Trametes versicolor, Phellinus linteus, Poria cocos, Antrodia camphorata, Flammulina velutipes, Pleurotus ostreatus, Pleurotus energyii,* and *Agaricus blazeii*, compounded as a tablet or within a capsule or powder dosage form and having a maximum cannabinoid dose per unit dosage form of 25 mg.

2. The cannabinoid oral dosage form in unit dosage form according to claim 1, wherein said hemp pomace contains cannabinoids including cannabidiol (CBD), cannabigerol (CBG) and tetrahydrocannabinol (THC) and further having a ratio of CBD or CBG to THC of between 60:1-120:1.

3. The oral dosage form of claim 1, wherein each oral dosage form contains less than 10% water as moisture and wherein said cannabinoid is one or more of cannabidiol, cannabigerol, cannabidivarin, cannabichromene, or cannabinol.

4. The oral dosage form of claim 1, wherein said hemp pomace co-fermented with said fungus is compounded as one or more tablets or capsules without separation of the hemp pomace or the co-fermentation products.

5. The oral dosage form of claim 1, wherein said dosage form contains no more than 10 mg cannabinoid per unit dosage form.

* * * * *